United States Patent [19]

Craig

[11] Patent Number: Plant 7,627

[45] Date of Patent: Aug. 20, 1991

[54] GERANIUM PLANT '208(81-344-3)'

[75] Inventor: Richard Craig, State College, Pa.

[73] Assignee: Research Corporation Technologies, Inc., Tucson, Ariz.

[21] Appl. No.: 382,504

[22] Filed: Jul. 18, 1989

[51] Int. Cl.[5] ..... A01H 5/00
[52] U.S. Cl. ..... Plt./68
[58] Field of Search ..... Plt./68

*Primary Examiner*—Howard J. Locker

*Attorney, Agent, or Firm*—Scully, Scott, Murphy & Presser

[57] ABSTRACT

This invention relates to a new and distinct cultivar of geranium (*Pelargonium*×*hortorum*) named #(81-344-3) substantially as described herein, characterized as having bright, luminescent scarlet flowers and being particularly well adapted to both commercial greenhouse production and garden performance, and as being early flowering, floriferous, self-branching, and compact.

1 Drawing Sheet

The present invention relates to a new and distinct cultivar of geranium (*Pelargonium*×*hortorum*) called '#208-(81-344-3)'. This cultivar has bright, luminescent, scarlet flowers, is early flowering, floriferous, self-branching, and compact. The cultivar is particualrly well adapted to both commercial greenhouse production and garden performance with excellent resistance to floral shattering.

The cultivar was developed from an organized, scientifically designed breeding program carried out at the Department of Horticulture, The Pennsylvania State University, University Park, Pa. 16802. This genotype resulted from the selection from progeny of the cross-pollination of geranium cultivars 'Honseler's Glorie Rot' and 'Karminball'. #208-(81-344-3)' differs from the previously patented cultivar #821-(82-116-13)' and its sib 'Centennial' basically through parentage. While the cultivars are similar in flower color, '#208-(81-344-3)' has a distinctive visible sheen to the petals producing a luminescnce. In addition floret size is generally larger than the previous cultivars and it produces significantly more florets per inflorescence than #821-(82-116-13)' and about the same as 'Centennial'. Petal number is similar to #821-(82-116-13)' but less than 'Centennial'. While maximum plant heights of test plants were similar, #208-(81-344-3)' will be slightly taller under optimum environmental conditions. The selection was asexually propagated by cuttings and the reproductions ran true.

BRIEF DESCRIPTION OF THE DRAWING

The FIGURE illustrates in color the cultivar including foliage and flowers.

With reference to the detailed description of the cultivar which follows, the test plant was grown in a glasshouse under full natural light, at a night temperature of approximately 58° F., and a day temperature of approximately 68° F. Soilless medium was fertilized with every watering with 200 ppm nitrogen from 15-16-17.

Color readings were taken under incandescent light at 200 foot candles and color identification was by reference to The Royal Horticultural Society Colour Charts, except where common terms of color definition are employed.

THE PLANT

Classification:

*Botanical.*—*Pelagronium*×*hortorum.*

*Tradename.*—#208-(81-344-3).

Form: Compact and self-branching.

Height: 18.5 cm; range 16.0–21.0 cm.

Growth: Free branching from base; short internodes; stands upright with no artificial support.

Leaves:

*Size.*—Largest leaf 5.5 cm long×9.0 cm wide Ratio of length to width approximately 2:3.

*Shape.*—Reniform, variously lobed.

*Margin.*—Crenate.

*Texture.*—Pubescent; dull.

*Color.*—Adaxial: Distal: Green 137A. Zone: Greyed-purple 187A overlaid with green 137A. Proximal: Green 137B. Abaxial: Green 137C.

*Ribs and veins.*—Palmate venation; veins recessed and prominent.

*Petioles.*—Texture: Lightly pubescent. Length: 8.0 to 9.2 cm. Color: Green 137C.

Stem:

*Internode length.*—1.9 to 2.1 cm.

*Color.*—Green 137C.

THE FLOWER

Blooming habit: Continuous.

Inflorescence form: Umbellate.

Inflorescence size: 10 cm across when florets are fully open.

Persistence: Persistent, non-shattering.

Disease resistance: Not known; favorable in outdoor trails.

Florets:

*Number.*—36 to 44.

*Form.*—Flat to cupped.

*Size.*—3.0–4.5 cm across open floret.

Petals:

*Number.*—6–8.

*Texture and appearance.*—Smooth with visible sheen.

*Color.*—Upper petals: Adaxial: Distal two-thirds: Red 44A. Proximal one-third: Red 38A with veins red 45B. Base: Small area of white 155D. Abaxial: Red group 41A with veins (red 45B); not as pronounced as on adaxial surface. Lower petals: Adaxial: Red 44A with veins (red 45b); less pronounced than on upper petal adaxial surface. Base white 155D. Abaxial Red 41A with basal veins and base white 155D.

Petaloids:

*Number.*—0, 1 or 2.

*Shape.*—Variable; often misshapen.

*Color.*—Similar of the color of the petals.

Sepals:

*Number.*—Usually 5.

Pedicel:

*Length.*—1.4–2.1 cm.

*Color.*—Yellow-green 144A, greyed-red 178A on distal end on mature florets.

Peduncle: Arises from node; opposed to leaf petiole; pubescent.

*Color.*—Yellow-green 144A.

*Length.*—13.0 to 15.2 cm.

Reproductive Organs

Androecium:

*Stamens.*—6–9 flat, ribbon-like filaments with rose-purple tips, joined at their bases; versatile attachment to anthers which are purple and well developed.

*Staminodes.*—At least 1 flat, ribbon-like filament with no anthers.

*Petaloid stamens.*—1–2 petal-like filaments with partially developed anthers.

Gynoecium:

*Pistil number.*—1. Length: 6.0–8.0 mm. Stigma: Purple. Style: Green. Ovary: 3.5–4.0 mm long; superior; very pubescent.

*Fruit.*—Achene schizocarp; rarely observed.

What is claimed is:

1. A new and distinct cultivar of geranium substantially as shown and described herein, characterized as having bright, luminescent scarlet flowers and being particularly well adapted to both commercial greenhouse production and garden performance and as being early flowering, floriferous, self-branching and compact.

* * * * *

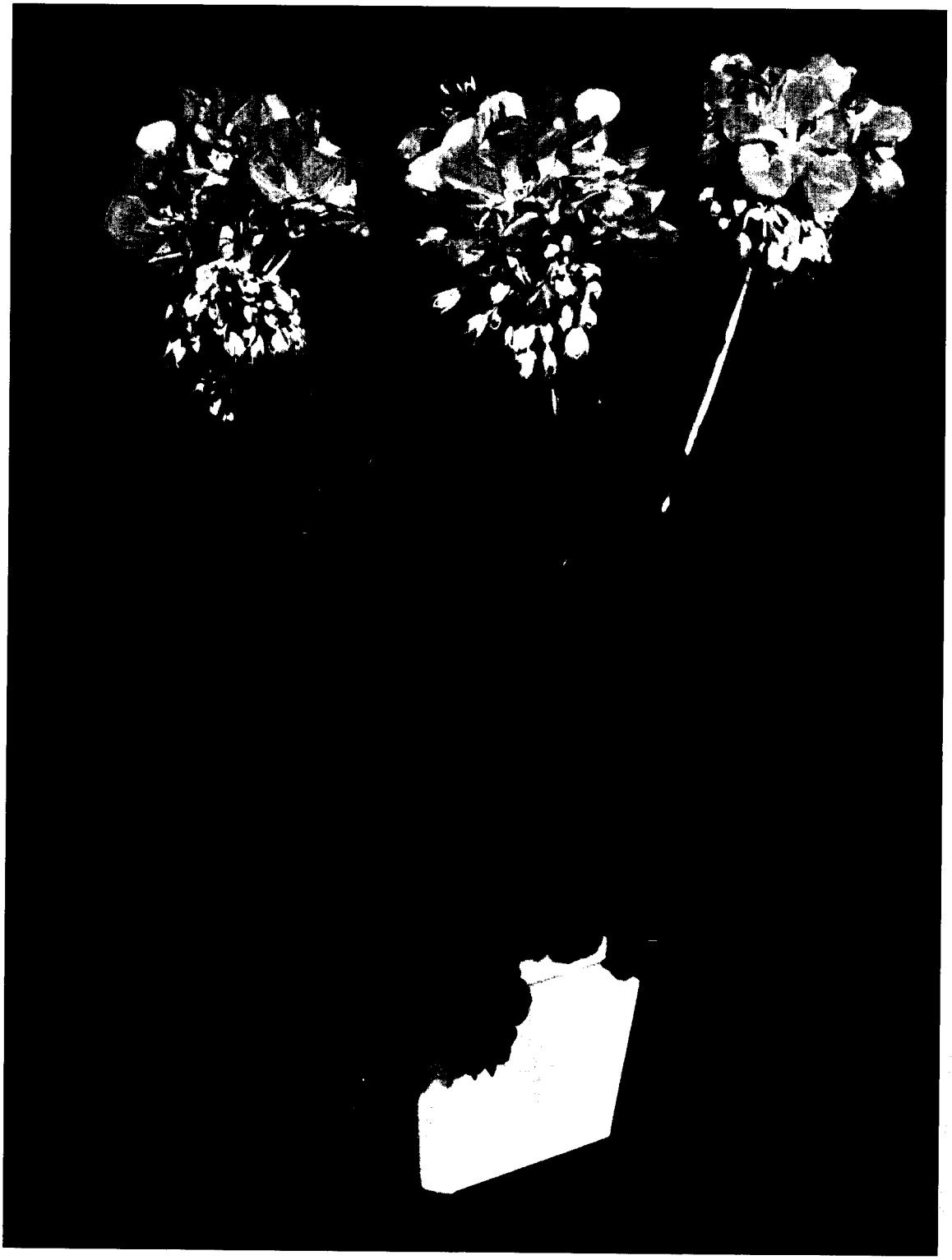

UNITED STATES PATENT AND TRADEMARK OFFICE

CERTIFICATE OF CORRECTION

PATENT NO. : Plant 7,627

DATED : August 20, 1991

INVENTOR(S) : Richard Craig

It is certified that error appears in the above-identified patent and that said Letters Patent is hereby corrected as shown below:

On the title page:

In the Abstract, line 2: "#(81-344-3)" should read as --#208-(81-344-3)--

Signed and Sealed this

Fourth Day of May, 1993

*Attest:*

Michael K. Kirk

MICHAEL K. KIRK

*Attesting Officer*

*Acting Commissioner of Patents and Trademarks*